(12) United States Patent
Cureington-Sims

(10) Patent No.: US 8,137,298 B2
(45) Date of Patent: Mar. 20, 2012

(54) ABSORBING MEDICAL BINDER SYSTEM AND METHOD

(75) Inventor: Christal Cureington-Sims, Austin, TX (US)

(73) Assignee: Core Corporations, LLC, Austin, TX (US)

( * ) Notice: Subject to any disclaimer, the term of this patent is extended or adjusted under 35 U.S.C. 154(b) by 288 days.

(21) Appl. No.: 12/473,042

(22) Filed: May 27, 2009

(65) Prior Publication Data

US 2009/0299258 A1    Dec. 3, 2009

Related U.S. Application Data

(60) Provisional application No. 61/135,228, filed on May 27, 2008.

(51) Int. Cl.
*A61F 13/06* (2006.01)
*A41D 13/00* (2006.01)
*A41C 1/00* (2006.01)

(52) U.S. Cl. ................ 602/61; 2/69; 450/140

(58) Field of Classification Search ........ 602/67, 602/61, 74, 60, 75–76, 79; 2/69, 401; 450/140, 450/155; 128/96.1, 99.1, 100.1
See application file for complete search history.

(56) References Cited

U.S. PATENT DOCUMENTS

| 5,158,541 | A | * | 10/1992 | McCurley | 602/79 |
| 5,520,980 | A | | 5/1996 | Morgan et al. | |
| 5,538,500 | A | | 7/1996 | Peterson | |
| 5,912,059 | A | | 6/1999 | Jones et al. | |
| 5,968,003 | A | * | 10/1999 | Sisson | 602/75 |
| 6,269,820 | B1 | | 8/2001 | Bays | |
| 6,270,469 | B1 | | 8/2001 | Mott | |
| 6,309,369 | B1 | | 10/2001 | Lebovic | |
| 7,425,171 | B2 | | 9/2008 | Maupin | |
| 2008/0039762 | A1 | * | 2/2008 | Johnson | 602/43 |

OTHER PUBLICATIONS

"Big Cinch" Internet webpage, available at <http://www.cinchtight.com/html/big_cinch.html>, May 6, 2009. (1 page).
"Big Cinch" brochure, accessed May 6, 2009. (2 pages).

* cited by examiner

*Primary Examiner* — Patricia Bianco
*Assistant Examiner* — Tarla Patel
(74) *Attorney, Agent, or Firm* — Meyertons, Hood, Kivlin, Kowert & Goetzel, P.C.; Eric B. Meyertons

(57) ABSTRACT

Provided is a method and system for bandaging an abdominal region of a patient. A method includes providing an abdominal binder and securing the abdominal binder about the abdominal region of a patient. The abdominal binder has an inner layer including an absorbent pad configured to contact and extend about at least a majority of the circumference of the abdominal region of a patient, and configured to absorb post-procedure fluids during use, and an outer layer including an elastic sheet of material for surrounding at least a portion of the inner layer and providing a compressive force to retain at least a majority of the inner layer against the abdominal region of the patient during use. The outer layer is about 70 to 130% of the size of the inner layer when the outer layer is provided in an unbiased state. The inner layer and the outer layer are coupled to one another at or near a first end of the inner layer and a first end of the outer layer, and a second end of the inner layer and a second end of the outer layer are configured to allow movement relative to one another.

29 Claims, 3 Drawing Sheets

# ABSORBING MEDICAL BINDER SYSTEM AND METHOD

PRIORITY

This patent application claims priority to U.S. Provisional Patent Application No. 61/135,228 filed May 27, 2008, the entirety of which is herein incorporated by reference.

BACKGROUND

1. Field of the Invention

The present invention generally relates to medical binders, and more particularly to systems and methods for providing a post-operative absorbing medical binder.

2. Description of Related Art

After certain medical procedures, such as abdominal and back surgeries, including liposuction on the abdominal, flanks and/or upper and lower back, a cesarean section, an appendectomy, gallbladder surgery, a hysterectomy, gastric bypass, or gastric banding, a patient may experience swelling and pain in the abdominal regions as well as a leakage of fluids from incisions made during the procedure. Typically, the patient is bandaged to help reduce the swelling, alleviate the pain and/or absorb the post-operative fluids. Often a compression garment or bandage (e.g., an abdominal binder) is provided that may be worn for an extended period, up to several weeks. In certain instances, the abdominal binder surrounds the abdominal region (e.g., the front and/or lower back region of the abdomen) of a patient to provide compressive support that helps the reduce swelling and alleviate pain in the abdominal region. Sometimes a separate absorbent pad is placed between the compression garment and the patient to absorb fluids, such as blood and injected fluids, such as saline.

Many medical binders are not designed to provide relief for certain post-operative conditions. For example, medical binders often include a wrap of material that provides support for to reduce swelling and alleviate pain, but they are not designed to absorb or otherwise dispose of leaked fluids. Even where an absorbent pad is placed between the medical binder and the patient's skin, the absorbent pads may move or slide around resulting in fluids, such as blood, seeping into and through the medical binder. This can lead to unsanitary conditions. Further, medical binders may be difficult to secure to the patient, leading to further discomfort and pain, and increasing the amount of time it takes to dress the patient. For instance, following a surgery such as liposuction, a patient may stand up from the medical table, exposing the open wounds, allowing a considerable amount of drainage to leak from the post-operative patient. The medical practitioner may place several absorbing pads around the patient and tape the pads together. The patient may also be asked to raise their arms and enter through a form of netting. Additional absorbing pads may be added to the open wounds and an elastic binder may be fitted around the patient to hold the absorbent pads. This process may be lengthy, jeopardize the procedure (e.g., from the absorbent pads moving, folding and wrinkling) and may be unsanitary, time consuming, and confusing for the patient to mimic when attempting to replace the dressing. Some medical binders may also be uncomfortable to wear, even when properly secured to the patient. For example, an edge of the medical binder may rub or otherwise irritate the patient's skin. Moreover, medical binders may not be designed to evenly distribute compressive forces across the affected area. For example, medical binders may result in an uneven distribution of forces (e.g., compression) against the patient's body that can result in stretching of the skin and/or folds and wrinkles in the skin. In the case of liposuction or similar procedures where a patient wears the medical binder for an extended period of time, uneven distribution of forces may result in undesirable conditions, such as permanent or semi-permanent lumps, folds and wrinkles at the surface of the skin.

Accordingly, there is a desire to provide a medical binder system and method that provides for absorption of fluids, is easily installed, is comfortable to the patient, and/or provides an even distribution of compressive force that may help to reduce the likelihood of lumps and fold/wrinkles.

SUMMARY

Various embodiments of an absorbing medical binder systems and related apparatus, and methods of operating the same are described. In one embodiment, a method of bandaging an abdominal region of a patient includes providing an abdominal binder and securing the abdominal binder about the abdominal region of a patient. The abdominal binder has an inner layer including an absorbent pad configured to contact and extend about at least a majority of the circumference of the abdominal region of a patient, and configured to absorb post-procedure fluids during use, and an outer layer including an elastic sheet of material for surrounding at least a portion of the inner layer and providing a compressive force to retain at least a majority of the inner layer against the abdominal region of the patient during use. The outer layer is about 70 to 130% of the size of the inner layer when the outer layer is provided in an unbiased state. The inner layer and the outer layer are coupled to one another at or near a first end of the inner layer and a first end of the outer layer, and a second end of the inner layer and a second end of the outer layer are configured to allow movement relative to one another.

In another embodiment, abdominal binder has an inner layer including an absorbent pad configured to contact and extend about at least a majority of the circumference of the abdominal region of a patient, and configured to absorb post-procedure fluids during use, and an outer layer including an elastic sheet of material for surrounding at least a portion of the inner layer and providing a compressive force to retain at least a majority of the inner layer against the abdominal region of the patient during use. The outer layer is about 70 to 130% of the size of the inner layer when the outer layer is provided in an unbiased state. The inner layer and the outer layer are coupled to one another at or near a first end of the inner layer and a first end of the outer layer, and a second end of the inner layer and a second end of the outer layer are configured to allow movement relative to one another.

In another embodiment, a method of bandaging an abdominal region of a patient includes providing an abdominal binder and securing the abdominal binder about the abdominal region of a patient. The abdominal binder has an inner layer including an absorbent pad configured to contact and extend about at least a majority of the circumference of the abdominal region of a patient, and configured to absorb post-procedure fluids during use, and an outer layer including an elastic sheet of material for surrounding at least a portion of the inner layer and providing a compressive force to retain at least a majority of the inner layer against the abdominal region of the patient during use. The outer layer is about 90 to 110% of the size of the inner layer when the outer layer is provided in an unbiased state. The inner layer and the outer layer are coupled to one another at or near a first end of the inner layer and a first end of the outer layer, and a second end of the inner layer and a second end of the outer layer are configured to allow movement relative to one another. Securing the abdominal binder about the abdominal region of a patient includes providing the inner layer about at least a portion of the abdominal region of the patient, stretching the outer layer around the abdominal region of the patient and about the inner layer, and securing a first end of the outer layer to a second end of the outer layer such that at least a portion of the abdominal binder completely encircles the abdominal region of the patient, and such that the stretched outer layer maintains a substantially even compressive force across the abdominal region of the patient.

BRIEF DESCRIPTION OF THE DRAWINGS

Advantages of the present invention will become apparent to those skilled in the art with the benefit of the following detailed description and upon reference to the accompanying drawings in which.

Figure 1:
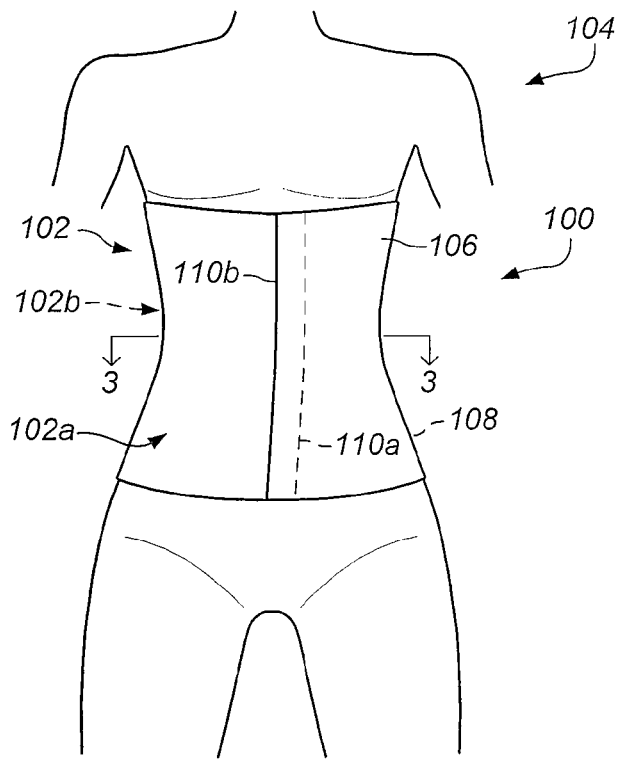
FIG. 1 is a perspective view that illustrates an absorbing medical binder secured about the abdominal region of a patient in accordance with one or more embodiments of the present technique.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF ILLUSTRATIVE EMBODIMENTS

As discussed in more detail below, certain embodiments of the present technique provided for a system and method that includes the use of an absorbing medical compression binder. In certain embodiments, the absorbing medical compression binder includes absorbent pads as well a compression garment. In some embodiments, the absorbing medical compression binder includes a stretch-type binder. In certain embodiments, the inside of the binder, is lined with the removable or non removable sterile or non sterile, absorbent pad. In some embodiments, the absorbing medical compression binder fits the abdominal region, and act as an absorbent as well as a compression garment. In some embodiments, the absorbing medical compression includes a stretch type-binder that is available in multiple different sizes (e.g., small, medium and large). In some embodiments, during use, the absorbing medical compression binder is immediately placed around the patient following surgery and is to be discarded or replaced as soon as the absorbent pads are full of fluid/blood. The ease of disposing of and/or replacing the absorbing medical compression binder may help to reduce the likelihood of mistakes when patients must change the binders on their own. In some embodiments, the absorbing medical compression binder provides an even distribution of absorption and pressure to help for maximum contouring.

FIG. 1 is a perspective view that illustrates an absorbent medical compression binder system ("medical binder system") 100 disposed about an abdominal region 102 of a patient 104 in accordance with one or more embodiments of the present technique. Abdominal region 102 includes the front abdominal region 102a extending from about the waist area to about the chest area, and includes a lower back region 102b of patient 104. In the illustrated embodiment, medical binder system 100 is secured about abdominal region 102 in a region between an upper region of pelvic bone and below an under-arm region and/or lower chest region of patient 104. Medical binder system 100 completely encircles (e.g., extends completely around) the abdominal region, including both front abdominal region 102a and lower back region 102b.

In one embodiment medical binder system 100 includes an outer layer 106 and an inner layer 108. In some embodiments, outer layer 106 provides support of abdominal region 102 that helps to inhibit swelling, to reduce pain and/or to retain inner layer 108. For example, in one embodiment, outer layer 106 may include an elastic (e.g., stretchable) material that can be secured/stretched around abdominal region 102 such that it exerts a compressive force. The compressive force may act inward toward patient 104, thereby inhibit swelling, reducing pain, and inhibiting inadvertent movement of inner layer 108. In one embodiment, outer layer 106 provides an even distribution of compressive force to facilitate contouring of the patient during recovery. For example, in the case of liposuction, the even compressive force may help reduce deformity (e.g., lumps, and wrinkles) that may otherwise form as a result of the dressing of the abdominal region. In one embodiment, even compression is provided by the homogeneous nature of outer layer 106 about its length. For example, outer layer may be of similar/even elasticity along its length such that it stretches substantially uniformly along its length.

In one embodiment, two ends of medical binder system 100 are fastened to one another to secure medical binder system 100 about patient 104 and/or to provide a sufficient compressive force. For example, in the illustrated embodiment, a second end 110b is wrapped/stretched around abdominal region 102 of patient 104 such that it overlaps first end 110a. The second end 110b may be secured at or near first end 110a to provide and maintain a compressive force. The compressive force may be increased or decreased by increasing or decreasing, respectively, the overlap between first end 110a and second end 110b.

In one embodiment, inner layer 108 is at least partially disposed between outer layer 106 and patient 104. For example, during use, inner layer 108 may be disposed such that it directly contacts skin of patient 104 and outer layer 106 may be disposed about inner layer 108 to hold inner layer 108 against the skin of patient 104. Other embodiments may include indirectly securing inner layer 108 against the skin of patient 104. For example, inner layer 108 may be disposed against clothing/bandages worn by patient 104 such that the clothing/bandages are located between at least a portion of inner layer 108 and the skin of patient 104.

In some embodiments, inner layer 108 may absorb fluids that leak or otherwise drain from patient 104. Fluids may include, post operative fluids such as blood, injectible fluids (e.g., saline), or various fluids that may be excreted or leaked from the patient 104 following a medical procedure. Inner layer 108 may be capable of absorbing and/or retaining about one cup, two cups, three cups or more of fluids. The absorption and retention of fluids may be sanitary as it draws the fluids away from a wound and/or the skin of patient 104. In one embodiment, inner layer 108 is capable of providing uniform absorption. For example, inner layer 108 may include a similar ability to absorb fluids across all or substantially all of its area.

In one embodiment, inner layer 108 includes an absorbent pad capable of absorbing and retaining the fluids such that they are inhibited from leaking onto other areas of patient 104, medical binder system 100, and/or the surrounding environment. In one embodiment, inner layer 108 includes a sterile absorbent pad suitable for use in a medical environment.

In some embodiments, one or more portions of medical binder 100 (e.g., inner layer 108) may be disposable and/or replaceable. Such an embodiment may be useful when inner layer 108 is saturated with fluid and needs to be replaced. For example, in an embodiment in which medical binder 100 is completely disposable, medical binder 100, including outer layer 106, may be removed from patient 104 and disposed of. In an embodiment in which inner layer 108 is replaceable and outer layer 106 is reusable, inner layer 108 may be removed from outer layer 106, and replaced with another inner layer 108. Outer layer 106 may be reused with the new, replacement inner layer.

Figure 2A:
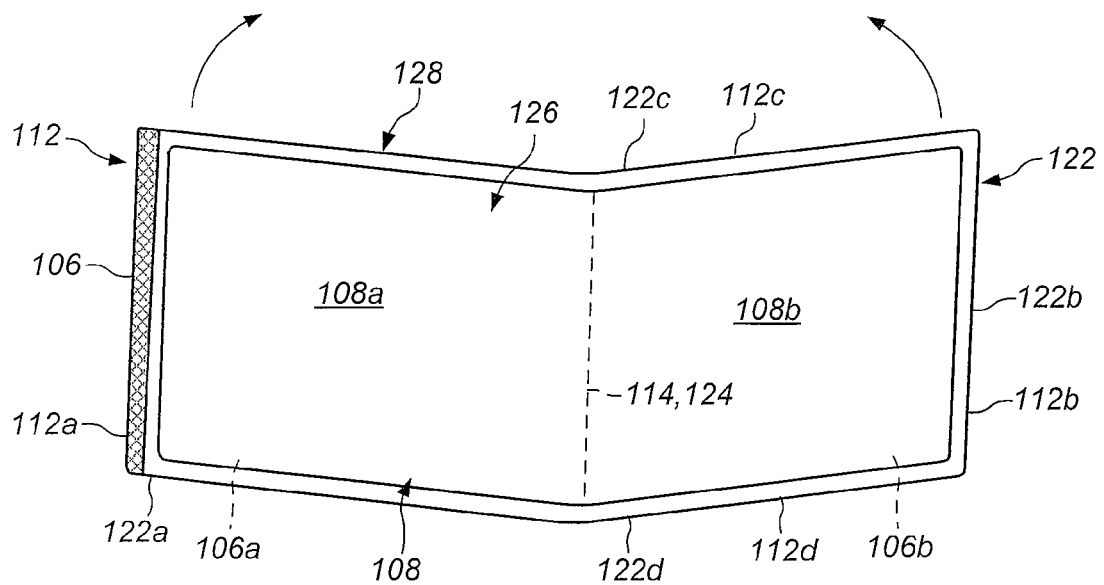
FIGS. 2A-2B are perspective views that illustrate the absorbing medical binder in accordance with one or more embodiments of the present technique.
Figure 2B:
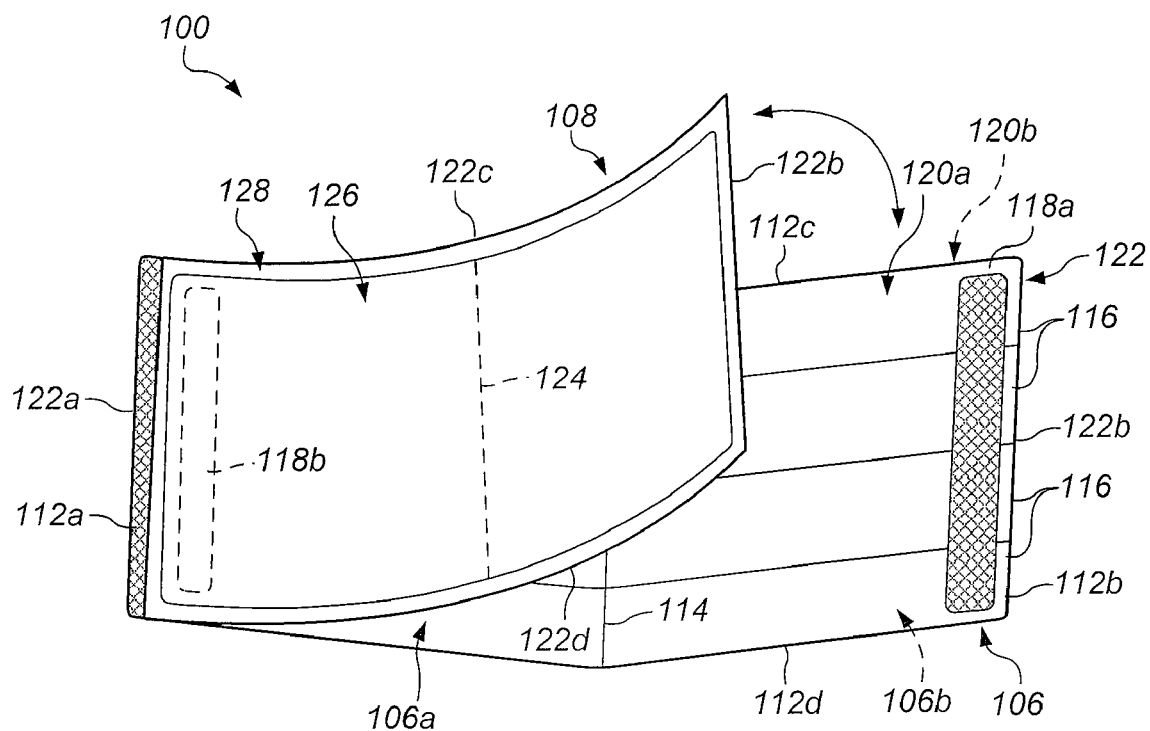

FIGS. 2A-2B illustrate medical binder 100, including outer layer 106 and inner layer 108, in accordance with one or more embodiments of the present technique. FIG. 2A includes an inside perspective view of medical binder 100 that includes inner layer 108 laid generally flat over outer layer 106. FIG. 2B includes a view of an inside of medical binder 100 that includes inner layer 108 peeled back from outer layer 106 such that an substantial portion of an inside surface of outer layer 106 is visible.

In the illustrated embodiment, outer layer 106 includes an elongated rectangular shaped sheet of material 112 having first end 112a proximate first end 110a of medical binder system 100, a second end 112b proximate second end 110b of medical binder system 100, and upper edge 112c and a lower edge 112d. Outer layer 106 may be formed from nylon, elastic, felt, or the like, or a combination thereof. A length of outer layer 106 may be defined by the distance between first end 112a and second end 112b. A height of outer layer 106 may be defined by the distance between upper edge 112c and lower edge 112d.

In one embodiment, outer layer 106 may have a length that is about that of the distance around abdominal region 102 of patient 104. For example, in one embodiment, a length of outer layer 106 may be anywhere in the range from about twenty-four inches to about sixty-two inches, or more. In one embodiment, outer layer 106 may have a height that is approximately the distance from a top of the pelvic bone to a just under the under-arm or chest area of patient 104. For example, in one embodiment, a height of outer layer 106 may be about six inches, seven inches, eight inches, nine inches, ten inches, eleven inches, twelve inches, thirteen inches, fourteen inches, fifteen inches or more.

In one embodiment, outer layer 106 includes a single sheet of material. In other embodiments, outer layer 106 may include multiple sheets/panels/strips of material. In one embodiment, outer layer 106 includes two generally rectangular panels coupled to one another along one of their ends. For example, as depicted in FIGS. 2A and 2B, outer layer 106 includes a first portion 106a proximate first edge 112a and a second portion 106b proximate second edge 112b that are coupled to one another at a seam 114. In one embodiment, first and second portions 106a and 106b may be fastened together via stitching at seam 114.

As depicted in FIG. 2B, in one embodiment, each of first portion 106a and 106b includes a panel composed multiple adjacent strips 116 of material oriented substantially horizontally between first and second ends 112a and 112b of outer layer 106. In one embodiment, each of strips 116 includes an elongated rectangular shaped elastic strip. In one embodiment, each of the sides of the elastic strips 116 is coupled to one another along their length such that they expand and contract together. An embodiment may include a separation of strips 116 along all, substantially all, or at least a portion of their length such that they can at least partially stretch independent of respective adjacent strips.

Figure 3:
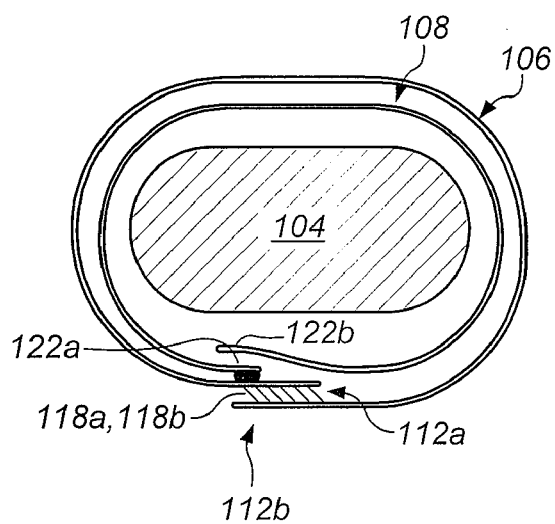
FIG. 3 is a cross-sectional view taken across line 3-3 of FIG. 1 that depicts the absorbing medical binder secured about the abdominal region of the patient in accordance with one or more embodiments of the present technique.

In one embodiment, first end 112a of outer layer 106 is fastenable to second end 112b of outer layer 106. For example, during use, ends 112a and 112b of outer layer may be coupled to one another to secure outer layer 106 about inner layer 108 and abdominal region 102 of patient 104. In one embodiment, a fastener and a complementary fastener are provided at or near one or both of first and second ends 112a and 112b of outer layer 106 such that ends of outer layer 106 may be coupled to one another. In the illustrated embodiment, a fastener 118a is provided at an inside surface 120 of outer layer 106 at or near second end 112a and a complementary fastener 118b is provided at an outside surface 120b of outer layer 106. During use, as depicted in FIG. 3, outside layer 106 may be wrapped around patient 104 such that inside surface 120a of second end 112b overlaps at least portion of outside surface 120b of first end 112a, thereby enabling fastener 118a to be coupled to complementary fastener 118b.

In one embodiment, fasteners 118a and/or complementary fastener 118b include one or more mechanical fasteners. For example, fastener 118a and/or 118b may include a hook and loop fastener, snaps/buttons, clips, or magnets. In one embodiment, at least one or both of fastener 118a and 118b includes VELCRO®. In such an embodiment, the VELCRO® may be coupled to outer layer 16 and/or inner layer 108 via stitching and/or an adhesive. In one embodiment, fastener 118a includes hook portions and complementary fastener 118b includes a loop portion of a hook-and-loop fastener, or vice versa. In one embodiment, fastener 118a and/or complementary fastener 118b may be integral with a portion of outside layer 106 and/or inside layer 108. For example, in one embodiment, rear surface 120b includes a texture (e.g., a loop type texture) complementary to hook fasteners such that hook-type fastener 118a may be coupled directly to surface 120b, or vice versa. Such an embodiment may enable coupling of fastener 118a and second end 112b at a variety of locations along surface 120b, thereby allowing outer layer 106 to be stretched at varying degrees around patient 104. For example, fastener 118a may be coupled anywhere along surface 120b of outer layer 106 providing a variable/infinite adjustment of medical binder system 100.

In the illustrated embodiment, inner layer 108 includes an elongated rectangular shaped sheet of material 122 having first end 122a proximate first end 110a of medical binder system 100, a second end 122b proximate second end 110b of medical binder system 100, and upper edge 122c and a lower edge 122d. A length of inner layer 108 may be defined by the distance between first end 122a and second end 122b. A height of inner layer may be defined by the distance between upper edge 122c and lower edge 122d.

In one embodiment, inner layer 108 includes one or more absorbent pads. For example, in the illustrated embodiment, inner layer 108 includes a single sheet of material that extends from first end 122a to second end 122b. In one embodiment, two or more absorbent pads may be coupled to one another to form inner layer 108. For example, in one embodiment, inner layer 108 includes two generally rectangular panels coupled to one another along one of their ends. For example, as depicted in FIGS. 2A and 2B, inner layer 108 may include a first portion 108a proximate first edge 122a and a second portion 108b proximate second edge 122b that are coupled to one another at a seam 124. In one embodiment, first and second portions 108a and 108b may be fastened together via an adhesive or stitching at seam 114.

In one embodiment, inner layer 108 includes one or more absorbent pads having a lining about an edge and/or a rear surface of the absorbent pad. For example, as depicted in FIGS. 2A and 2B, inner layer 108 includes an absorbent pad 126 surrounding by a lining 128. In one embodiment, lining 128 may include a generally impermeable material, such as thin plastic sheeting. In one embodiment, lining 128 also extends around a rear surface of inner layer 108 such that it is positioned between inner layer 108 and inner surface 120a of outer lay 106 during use. Lining 128 located on a rear surface of inner layer 108b may inhibit absorbed fluids from contacting or otherwise leaking through onto outer layer 106 or other portions of the surrounding environment. Lining 128 located around the edges of absorbent pad 126 may help to contain fluids in the absorbent pad 126 such that they do not leak from edges of absorbent pad 126. For example, lining 128 may form a trough around the edges of absorbent pad 126 that fluids may collect in. Lining 128 may also provide support for absorbent pad 126. For example, lining 128 located around the edges as well as on the rear surface of inner layer 108 may inhibit tearing of absorbent pad 126. In some embodiments, lining 128 may include a relatively smooth or slick material/coating that enables inner layer to move/slide relative to inner surface 120a of outer layer 106. For example, a rear surface of inner layer 108 facing outer layer 106 during use may include a thin-smooth plastic sheet of material that inhibits absorbent pad 126 from contacting outer layer 106. Such movement/sliding may allow inner layer and outer layer to move substantially independent of one another, thereby helping to inhibit the formation of folds or wrinkles in inner layer 108. In one embodiment, lining 128 includes a relatively soft material that is comfortable to the touch. In one embodiment, lining 128 lining provided around edges of absorbent pad 126 contacts the skin of patient 104 during use and/or inhibits edges of absorbent pad 128 from contacting the skin of patient 104. Such an embodiment may help to reduce irritation that may otherwise be caused at the edges of inner layer 108.

In some embodiments, at least a portion of inner layer 108 is coupled to outer layer 106. In one embodiment, one end of inner layer 108 is directly fixed relative to an end of outer layer to an end of outer layer 106. For example, in the illustrated embodiment, first end 122a of inner layer 108 is coupled to first end 112a of outer layer 106. In another embodiment, first end 122a may be coupled near first end 112a. For example, first end 122a may be coupled within about one, two, three, four, five, six, seven, eight, nine, ten inches of first end 112a. In the illustrated embodiment, the other edges, including the second end 122b, the upper edge 122c and the lower edge 122d are not directly fixed relative to another portion of outer layer 106. For example, second end 122b, upper edge 122c and lower edge 122d of inner layer 108 are not directly coupled to second end 112b, upper edge 112c and lower edge 112d of outer layer 106, respectively. In such an embodiment, although inner layer 108 is fixed at one end to outer layer 106, substantially all, or at least a majority, of the area of inner layer 108 is able to move/slide freely with respect to outer layer 106. Such movement/sliding may allow inner layer and outer layer to move substantially independent of one another to help inhibit the formation of folds or wrinkles in inner layer 108 and the skin of patient 104. Further movement/sliding enable outer layer 106 to slide relative to inner layer 108 and or the skin of patient 104 to allow outer layer 106 to maintain an even compressive force/pressure about abdominal region 102, thereby helping to provide contouring of patient 104 while inhibiting the formation of wrinkles and folds in inner layer 108 and the skin of patient 104. The non-fixed (e.g., uncoupled) configuration of second end 122b also enables inner layer 108 to be folded inside of first ends 112a and 122a, during use, as depicted and described with respect to FIG. 3.

In some embodiments, one or more other portions of inner layer 106 may be directly fixed relative to a portion of outer layer 108. For example, at least a portion of second end 122b, upper edge 122c and/or lower edge 122d of inner layer 108 may be coupled to or near second end 112b, upper edge 112c and lower edge 112d of outer layer 106, respectively. Fixing one or more portion inside layer 108 to outside layer 106 may help to prevent bunching and/or disfiguration of inside layer 108 while still allowing outside layer 106 to stretch to fit around abdominal region 102 of patient 104.

In one embodiment, coupling between inner layer 106 and outer layer 108 may include non-removably coupling or removably coupling. Non-removably coupling may include coupling two or more components such that are not designed to be uncoupled/separated from one another. Removably coupling may include coupling two or more components that are designed to be uncoupled/separated from one another. For example, in one embodiment non-removably coupling first edge 122a of inner layer 108 and first edge 112a of outer layer 106 may include stitching them together. In another embodiment removably coupling edge 122a of inner layer 108 and first edge 112a of outer layer 106, they may include coupling them together with hook-and-loop fasteners (e.g., VELCRO®), snaps, buttons, clips, and the like. In another embodiment removably coupling may include the use of an adhesive backing. For instance, inner layer 108 may include an adhesive backing on its rear/outer surface at or near first end 122a that is adhered to a complementary portion of an inner surface 120a at or near first end 112a of outer layer 106. Other embodiments may include any combination of non-removably coupling and/or removably coupling one or more portions of inner layer 108 to outer layer 106.

In one embodiment, inner layer 108 may have a length that is about that of the distance around abdominal region 102 of patient 104. For example, in one embodiment, a length of inner layer 106 may be anywhere in the range from about twenty-four inches to about sixty-two inches, or more. In one embodiment, inner layer 108 may be sized such that it can be disposed about at least a majority of the circumference of the abdominal region of the patient. For example, inner layer 108 may have a length that enables it to be disposed about 50%, 60%, 70%, 80%, 90%, 95%, ore more of abdominal region 102 of patient 104. In one embodiment, inner layer 108 may have a height that is approximately the distance from a top of the pelvic bone to a just under the under-arm or chest area of patient 104. For example, in one embodiment, a height of inner layer 108 may be about six inches, seven inches, eight inches, nine inches, ten inches, eleven inches, twelve inches, thirteen inches, fourteen inches, fifteen inches or more.

In one embodiment, inner layer 108 and outer layer 106 may be approximately the same size. For example, in one embodiment where inner layer 108 and outer layer 106 are about the same size, inner layer 108 may be about 80% to 120% or about 90% to about 110% of the size of outer layer 106. As depicted in FIGS. 2A and 2B inner layer 108 and outer layer 106 may have about the same length and width such that when medical binder system 100 is laid out flat, first end 122a, second end 122b, upper edge 122c and lower edge 122d of inner layer 108 align with first end 112a, second end 112b, upper edge 112c and lower edge 112d of outer layer 106. In such an embodiment there is little to no overlap at each of the edges.

In one embodiment, inner layer 108 may have as area that is half the size of an area of outer layer 106 or greater. For example, inner layer 108 may have an area that is about 50%, 60%, 70%, 80%, 90%, 95%, 100%, 105%, 110% 120% or more, of the area of outer layer 106. Such relative area may help to ensure that inner layer 108 is capable of absorbing fluids over a majority or all of abdominal region 102. For example, inner layer 108 may cover at least front abdominal area 102a and/or lower back area 102b during use.

In one embodiment, inner layer 108 may be sized such that it covers a majority or all of the area between outer layer 106 and abdominal region 102 during use (e.g., coverage area). For example, inner layer 108 is provided between outer layer 106 and patient 104 such that a portion of inner layer 108 is disposed between a majority of an inner surface 120a and skin of patient 104. Such an embodiment may help inhibit a majority or all contact of outer layer 106 with abdominal region 102 during use, thereby reducing the likelihood of irritation and helping to ensure fluids are absorbed into the pad and do not leak into outer layer 106. In one such embodiment, inner layer 108 covering all of the area between the inner surface 120a and skin of patient 104 may be said to cover 100% of the outer layer 106. In one embodiment, inner layer 108 may be sized such that it covers less than all of outer layer 106 during use. For example, inner layer 108 may provide coverage of about 50%, 60%, 70%, 80%, 90% 95%, or more of the area between outer layer 106 and abdominal region 102 during use.

Figure 4:
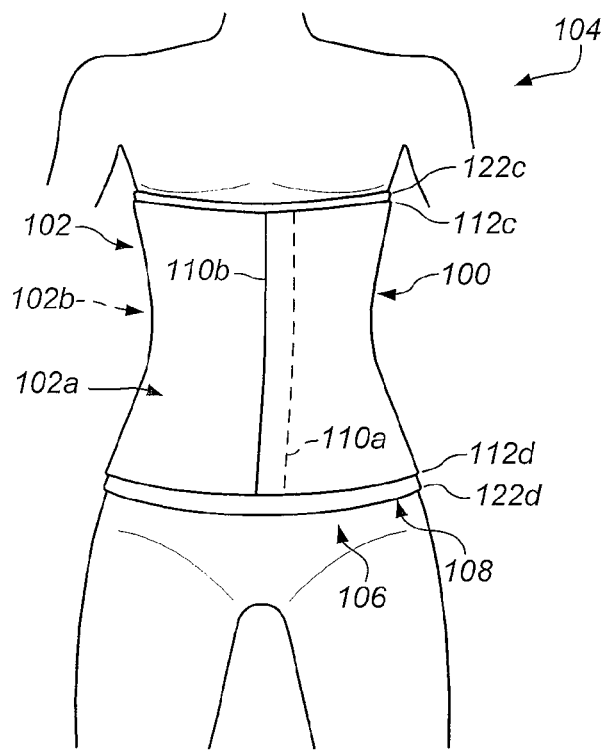
FIG. 4 is a perspective view that illustrates the absorbing medical binder secured about the abdominal region of a patient in accordance with one or more embodiments of the present technique.

In one embodiment, inner layer 108 and outer layer 106 may have sizes and/or certain dimensions that are different. For example, inner layer 108 may have a length and/or width that are greater that the length and/or width of outer layer 106. In one embodiment, a height of inner layer 108 is greater than a height of outer layer 106. In such an embodiment, upper edge 122c and or lower edge 122d of inner layer 108 may extend beyond upper edge 112c and lower edge 112d of outer layer 106. For example, as depicted in FIG. 4, in one embodiment, both upper edge 122c and lower edge 122d of inner layer 108 may extend beyond upper edge 112c and lower edge 112d of outer layer 106. In such an embodiment, inner layer 108 extending beyond the edges of outer layer 106 may inhibit outer layer (e.g., edges 112c and 112d) from directly contacting skin of patient 104, thereby reducing a likelihood of irritation to patient 104. In one embodiment, extending a portion of inner layer 108 beyond the edges of outer layer 106 may provide a region of collecting fluids. For example, fluids that are absorbed into inner layer 108 may be forced due to compression of outer layer 106 toward the upper and lower edges and collect at the edge of inner layer 108. Gravity may also act to draw fluids toward the lower edges. In some embodiments, only one of the lower and upper edges 122c and 122d may extend past the upper and lower edges 112c and 112d of outer layer 106. For example, in one embodiment, only upper edge 112c or lower edge 112d may extend beyond upper edge 112c or lower edge 112d, respectively.

In one embodiment, a length of inner layer 108 is greater than a height of outer layer 106. For example, in one embodiment, inner layer 108 is longer than outer layer 106 such that second edge 122b of inner layer 108 extends beyond second edge 112b of outer layer 106, when they are laid flat, as depicted in FIG. 2A. In one embodiment, first end 122a of inner layer 108 may be positioned such that it extends beyond first edge 112a of outer layer. Such embodiments, may enable second edge 122b to completely encircle abdominal region 102 of patient 104 and also cover an attachment region 130 (e.g., proximate where first end 112a of outer layer 106 is attached to second end 112b during use). This may enable the inner layer to inhibit outer layer 106 from contacting skin of patient 104 during use, thereby reducing the likelihood of irritation at the attachment region. Further, this may enable inner layer to provide a completely or substantially complete coverage that prevents fluids from leaking onto outer layer 106 and/or the surrounding environment.

In one embodiment, a length of inner layer 108 is less than a height of outer layer 106. For example, in one embodiment, outer layer 106 is longer than inner layer 108 such that second edge 112b of outer layer 106 extends beyond second edge 122b of inner layer 108, when they are laid flat, as depicted in FIG. 2A. Such an embodiment may enable second edge 112b to completely encircle abdominal region 102 of patient 104 such that it can be wrapped around exterior surface 120b of first end 112a. This may enable outer layer 106 to easily be secured to about patient 104.

In one embodiment, medical binder 100 includes a generally rectangular shape. For example, as depicted in FIGS. 2A and 2B, medical binder includes a generally rectangular shape that includes two panels joined at a slight angle relative to one another. The slight angle at seam 114 may provide a shape that conforms to a shape of abdominal region 102. In one embodiment, the two panels are positioned at about an angle of about one, two three, four, five, six, seven, eight, nine, ten, eleven, twelve, thirteen, fourteen, fifteen or more degrees relative to one another. In one embodiment, one or both of inner layer 108 and outer layer 106 may include a rectangular shaped without a seam or similar angled feature. Other embodiments may include various features, such as curvatures that are conducive to fit about patient 104. For example, cut-outs and/or curvatures in upper and lower edges may be provided under the underarm are, the chest, and/or above the pelvic/hip regions.

In one embodiment, medical binder 100 may be provided in one or more sizes to accommodate patients of varying sizes, ages, genders, and the like. For example, medical binder 100 may be sized to fit the patients including but not limited to the following:

| Female | 24"-30" | S |
| Female | 30"-38" | M |
| Female | 38"-46" | L |
| Female | 46"-54" | XL |
| Female | 46"-54" | XXL |
| Female | 54"-62" | XXXL |
| Male | 24"-30" | S |
| Male | 30"-38" | M |
| Male | 38"-46" | L |
| Male | 46"-54" | XL |
| Male | 54"-62" | XXL. |

Figure 5:
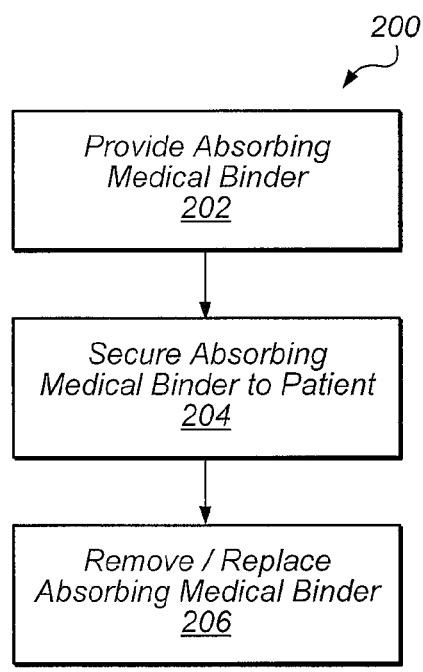
FIG. 5 is a flow chart that illustrates a method of using the absorbent medical binder in accordance with embodiments of the present technique.

FIG. 5 is a flowchart that illustrates a method 200 of using absorbing medical binder 100 in accordance with one or more embodiments of the present invention. The method includes providing a medical binder, as depicted at block 202. In one embodiment, providing the absorbing medical binder includes providing a medical binder in accordance with any-one of the embodiments described herein and/or having any combination of features described herein. In one embodiment, the absorbing medical binder is provided in a hermetically sealed package at or shortly after a time of the medical procedure. In one embodiment, the absorbing medical binder is provided with an inner layer already coupled to the outer layer. In another embodiment, such as an embodiment in which the inner layer is disposable/replaceable, the outer layer and inner layer may be provided separately and the inner layer may be coupled to the outer layer at or near the time of use. For example, inner layer may be coupled/assembled to outer layer before during or after surgery. In one embodiment, the absorbing medical binder may be provided as a kit that include two or more inner layers that can be used with the provided outer layer.

Method 200 also includes securing the absorbing medical binder to the patient, as depicted at block 204. In one embodiment, the absorbing medical binder may be provided such that it can be installed immediately after surgery or a similar medical procedure. In one embodiment, securing the absorbing medical binder to the patient include wrapping a first end of the absorbing medical binder about the abdominal region of the patient and coupling the first end to a second end of the absorbing medical binder such that it completely encircles the abdominal region (e.g., the front abdominal region and lower back region) of the patient. In one embodiment, coupling of the first end to the second end is provided at a front side of the patient (e.g., near the front abdominal region). Other embodiments may include coupling the first and second ends in the lower back region or on either one of the sides of the patient. In one embodiment, coupling of the first end includes coupling a hook-and-loop fastener, as described above. Other embodiments may include the use of snaps, clips, an adhesive, tape, or any combination thereof. In one embodiment, securing the absorbing medical binder includes placing the inner layer between the outer layer and the patient such that more than about a majority or more (e.g., all) of the outer layer is covered by the inner layer such that the outer layer is inhibited from contacting the patient directly. In one embodiment, at least one ends of the inner layer is tucked inside of the attachment region and overlap one another to help ensure a portion of the outer layer at or near the attachment region does not directly contact the patient. Some embodiments may include securing the medical binder to the patient at times other than immediately after surgery. For example, a new or replacement medical binder may be secured to the patient at a later time (e.g., when the inner layer is saturated with fluids).

Method 200 also includes removing and/or replacing the absorbing medical binder, as depicted at block 206. Removing/replacing the absorbing medical binder may be done when the medical binder is saturated with fluid (e.g., every few hours), when leakage has stopped/slowed (e.g., after twenty-four to forty-eight hours), when compressive support is no longer needed, and/or the absorbent medical binder needs to be removed for some other reason (e.g., observation by a medical practitioner). In one embodiment, removing and/or replacing the absorbing medical binder may include removing the absorbing medical binder from the abdominal region of the patient, and discarding the entire absorbing medical binder or discarding and replacing only a portion of the absorbing medical binder. For example, in one embodiment, when the inner layer of the absorbing medical binder is saturated with fluid or otherwise needs to be replaced, the absorbing medical binder may be removed and the entire medical binder, including the inner layer and the outer layer, may be discarded. Another medical binder (e.g., a new medical binder) may be provided and secured to the patient, as described with respect to steps 202 and 204. In another embodiment, when the inner layer of the absorbing medical binder is saturated with fluid or otherwise needs to be replaced, the absorbing medical binder may be removed from the patient, and the inner layer and outer layer separated from one another (e.g., uncoupled from one another). For example, in an embodiment in which the inner layer is coupled to the outer layer via hook-and-loop fastening, the inner layer may simply be pulled apart from the other layer. A replacement inner layer (e.g., a new absorbent pad) may be provided and coupled to the previously used outer layer (e.g., the elastic/stretchable sheet). For example, in an embodiment in which the inner layer is coupled to the outer layer via hook-and-loop fastening, the fastener of the inner layer may simply be pressed against the complementary fastener of the other layer. In such an embodiment, the outer layer is reusable and the inner layer is disposable/replaceable. Once the medical binder has been discarded and another complete absorbent medical binder has been provided or the inner layer of the existing medical binder has been replaced, the new/replaced absorbent medical binder may be and secured to the patient, as described with respect to steps 202 and 204. Such a process may be repeated as necessary.

Other embodiments may include any combination of the above described features. In one embodiment, multiple inner layer may be exchanged with an outer layer several times, and the outer layer may be discarded and replaced. For example, the complete absorbent medical binder may be discarded and replaced after a given number (e.g., three) inner layers have been exchanged/replaced with the outer layer.

Although certain embodiments have been discussed in detail with regard to the abdominal region, other embodiments of the system 10 are within the scope of this disclosure. For example similar medical binders may be provided for other portions of the human body (e.g., the leg, arm, neck). Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Furthermore, note that the word "may" is used throughout this application in a permissive sense (i.e., having the potential to, being able to), not a mandatory sense (i.e., must). The term "include", and derivations thereof, mean "including, but not limited to". As used in this specification, the singular forms "a", "an" and "the" include plural referents unless the content clearly indicates otherwise. Thus, for example, reference to "a binder" includes a combination of two or more binders. The term "coupled" means "directly or indirectly connected".

What is claimed is:
1. A method of bandaging an abdominal region of a patient, comprising:
    providing an abdominal binder comprising:
        an inner layer comprising an absorbent pad that, during use, contacts and extends about at least a majority of the circumference of the abdominal region of a patient, and that absorbs post-procedure fluids during use; and an outer layer comprising an elastic sheet of material that, during use, surrounds at least a portion of the inner layer, and that provides a compressive force to retain at least a majority of the inner layer against the abdominal region of the patient during use, wherein the outer layer is substantially 70 to 130% of the size of the inner layer when the outer layer is provided in an unbiased state, and wherein the inner layer and the outer layer are coupled to one another at or near a first end of the inner layer and a first end of the outer layer, and a second end of the inner layer and a second end of the outer layer, during use, allow movement relative to one another; and securing the abdominal binder about the abdominal region of a patient.

2. The method of claim 1, wherein securing the abdominal binder about the abdominal region of the patient comprises providing the inner layer about at least a portion of the abdominal region of the patient, stretching the outer layer around the abdominal region of the patient and about the inner layer, and securing a first end of the outer layer to a second end of the outer layer such that the stretched outer layer maintains a compressive force about at least a portion of the abdominal region of the patient.

3. The method of claim 1, wherein securing the abdominal binder about the abdominal region of the patient comprises securing a first end of the outer layer to a second end of the outer layer such that at least a portion of the abdominal binder completely encircles the abdominal region of the patient, and such that a substantially even compressive force is distributed across at least a portion of the abdominal region of the patient.

4. The method of claim 3, wherein the substantially even compressive force distributed across the abdominal region of the patient comprises a smooth distribution of forces across at least a portion of the abdominal region of the patient that inhibits the formation of wrinkles and/or folds along the surface of at least a portion of the skin of the patient.

5. The method of claim 1, wherein securing the abdominal binder about the abdominal region of a patient comprises extending a lower edge of the inner layer below a lower edge of the outer layer such that the compressive force of the outer layer, during use, allows absorbed post-procedure fluids to collect in a portion of the lower edge of the inner layer that extends below the lower edge of the outer layer.

6. The method of claim 1, wherein the inner layer comprises an inner layer height that extends between a lower and upper edge of the inner layer, and that is greater than an outer layer height that extends between a lower and upper edge of the outer layer of the outer layer, and wherein securing the abdominal binder about the abdominal region of a patient comprises extending the lower edge and the upper edge of the inner layer beyond the lower and upper edge of the outer layer, respectively, such that at least a majority of the lower edge and the upper edge of the outer layer does not directly contact skin of the patient.

7. The method of claim 1, wherein the first end of the inner layer and the first end of the outer layer are removably coupled to one another.

8. The method of claim 1, further comprising uncoupling the first end of the inner layer and the first end of the outer layer and coupling a first end of a replacement inner layer to the first end of the outer layer.

9. The method of claim 1, wherein a second end of the inner layer and a second end of the outer layer are not coupled to one another.

10. The method of claim 1, wherein a lower edge of the inner layer and a lower edge of the outer layer, during use, allow movement relative to one another, and wherein an upper edge of the inner layer and an upper edge of the outer layer, during use, allow movement relative to one another.

11. The method of claim 1, wherein a lower edge of the inner layer and a lower edge of the outer layer are not coupled to one another, and wherein an upper edge of the inner layer and an upper edge of the outer layer are not coupled to one another.

12. The method of claim 1, wherein the inner layer and the outer layer each comprise a rectangular shape having a length that, during use, completely encircles the abdominal region of the patient during use.

13. The method of claim 1, securing the abdominal binder about the abdominal region of a patient provides an even distribution of compressive force across at least a portion of the abdominal region of the patient inhibits formation of wrinkles and/or folds along the surface of at least a portion of the skin of the patient.

14. An abdominal binder, comprising:
an inner layer comprising an absorbent pad that, during use, contacts and extends about at least a majority of the circumference of the abdominal region of a patient, and that absorbs post-procedure fluids during use; and an outer layer comprising an elastic sheet of material that, during use, surrounds at least a portion of the inner layer, and that, during use, provides a compressive force to retain at least a majority of the inner layer against the abdominal region of the patient during use, wherein the outer layer is substantially 70 to 130% of the size of the inner layer when the outer layer is provided in an unbiased state, and wherein the inner layer and the outer layer are coupled to one another at or near a first end of the inner layer and a first end of the outer layer, and a second end of the inner layer and a second end of the outer layer, during use, allow movement relative to one another.

15. The abdominal binder of claim 14, wherein the inner layer and the outer layer are removably coupled to one another at or near the first end of the inner layer and the first end of the outer layer.

16. The abdominal binder of claim 15, wherein the inner layer and the outer layer are coupled to one another via an adhesive and/or a mechanical fastener.

17. The abdominal binder of claim 14, wherein a second end of the inner layer and a second end of the outer layer are not coupled to one another.

18. The abdominal binder of claim 14, wherein a lower edge of the inner layer and a lower edge of the outer layer, during use, allow movement relative to one another, and wherein an upper edge of the inner layer and an upper edge of the outer layer, during use, allow movement relative to one another.

19. The abdominal binder of claim 18, wherein a lower edge of the inner layer and a lower edge of the outer layer are not coupled to one another, and wherein an upper edge of the inner layer and an upper edge of the outer layer are not coupled to one another.

20. The abdominal binder of claim 14, wherein a lower edge of the inner layer, during use, extends below a lower edge of the outer layer such that the compressive force of the outer layer causes absorbed post-procedure fluids to collect in a portion of the lower edge of the inner layer that extends below the lower edge of the outer layer.

21. The abdominal binder of claim 14, wherein the inner layer and the outer layer each comprise a rectangular shape having a length that, during use, completely encircles the abdominal region of the patient during use.

22. The abdominal binder of claim 14, wherein the outer layer provides a substantially even compressive force is distributed across at least a portion of the abdominal region of the patient during use.

23. The abdominal binder of claim 14, wherein a first end of the outer layer comprises a first fastener and the second of the outer layer comprises a second fastener that, during use, couples to the first fastener.

24. The abdominal binder of claim 14, wherein the outer layer comprises two panels coupled to one another at an angle relative to one another, wherein the angle, during use, conforms to the shape of the abdominal region of the patient during use.

25. A method of bandaging an abdominal region of a patient, comprising:
 providing an abdominal binder comprising:
  an inner layer comprising an absorbent pad that, during use contacts and extends about at least a majority of the circumference of the abdominal region of a patient, and absorbs post-procedure fluids during use; and
  an outer layer comprising an elastic sheet of material that, during use, surrounds at least a portion of the inner layer, and provides a compressive force to retain at least a majority of the inner layer against the abdominal region of the patient during use,
  wherein the inner layer is about 90 to 110% of the size of the outer layer when the outer layer is provided in an unbiased state, and
  wherein the inner layer and the outer layer are coupled to one another at or near a first end of the inner layer and a first end of the outer layer, and a second end of the inner layer and a second end of the outer layer, during use, allow movement relative to one another; and
 securing the abdominal binder about the abdominal region of a patient, wherein securing the abdominal binder about the abdominal region of the patient comprises:
 providing the inner layer about at least a portion of the abdominal region of the patient;
 stretching the outer layer around the abdominal region of the patient and about the inner layer; and
 securing a first end of the outer layer to a second end of the outer layer, such that at least a portion of the abdominal binder completely encircles the abdominal region of the patient, and such that the stretched outer layer maintains a substantially even compressive force across the abdominal region of the patient.

26. A method of bandaging an abdominal region of a patient, comprising:
 providing an abdominal binder comprising:
  an inner layer comprising an absorbent pad that, during use, contacts and extends about at least a majority of the circumference of the abdominal region of a patient, and that absorbs post-procedure fluids during use; and
  an outer layer comprising an elastic sheet of material that, during use, surrounds at least a portion of the inner layer, and provides a compressive force to retain at least a majority of the inner layer against the abdominal region of the patient during use,
  wherein the inner layer is substantially 70 to 130 percent of the size of the outer layer when the outer layer is provided in an unbiased state, and
  wherein the inner layer and the outer layer are coupled to one another at or near a first end of the inner layer and a first end of the outer layer, and a second end of the inner layer and a second end of the outer layer allow movement relative to one another during use; and
 securing the abdominal binder about the abdominal region of a patient such that a substantially even compressive force is distributed across at least a portion of the abdominal region of the patient.

27. The method of claim 26, wherein the substantially even compressive force are distributed across the abdominal region of the patient such that a smooth distribution of forces across the abdominal region of the patient inhibits formation of wrinkles and/or folds along the surface of at least a portion of the skin of the patient.

28. An abdominal binder, comprising:
 an inner layer comprising an absorbent pad that, during use, contacts and extends about at least a majority of the circumference of the abdominal region of a patient, and that absorbs post-procedure fluids during use; and
 an outer layer comprising an elastic sheet of material that, during use, surrounds at least a portion of the inner layer, and that, during use, provides a compressive force to retain at least a majority of the inner layer against the abdominal region of the patient during use,
 wherein the outer layer is substantially 70 to 130% of the size of the inner layer when the outer layer is provided in an unbiased state,
 wherein the inner layer and the outer layer are coupled to one another at or near a first end of the inner layer and a first end of the outer layer, and a second end of the inner layer and a second end of the outer layer, during use, allow movement relative to one another; and
 wherein the outer layer provides a substantially even compressive force distributed across at least a portion of the abdominal region of the patient during use.

29. The binder of claim 28, wherein the substantially even compressive force are distributed across the abdominal region of the patient such that a smooth distribution of forces across the abdominal region of the patient inhibits formation of wrinkles and/or folds along the surface of at least a portion of the skin of the patient.

* * * * *